United States Patent [19]

Charlton et al.

[11] Patent Number: 4,968,630

[45] Date of Patent: Nov. 6, 1990

[54] SELECTIVITY IMPROVEMENT FOR LITHIUM ION TESTS

[75] Inventors: Steven C. Charlton, Osceola, Ind.; James B. Denton, Montclair, N.J.

[73] Assignee: Miles Inc., Elkhart, Ind.

[21] Appl. No.: 388,813

[22] Filed: Aug. 3, 1989

[51] Int. Cl.$^5$ ............................................. G01N 21/00
[52] U.S. Cl. ...................................... 436/79; 436/74; 436/169; 422/56; 422/68
[58] Field of Search ...................................... 436/74, 79

[56] References Cited

PUBLICATIONS

Fedorov, N. A., "Levels of free pyrimidines and purines in rat liver and incorporation of carbon-14 labeled sodium bicarbonate into these compounds under the action of a single Intraperitoned injection of orotic acid", Vop. Med. Khim., 17(3), pp. 260–263, 1971.

*Primary Examiner*—Robert J. Warden
*Assistant Examiner*—David Redding
*Attorney, Agent, or Firm*—Roger N. Coe

[57] ABSTRACT

A method and apparatus for determining lithium ion concentrations in an aqueous sample are provided wherein the selectivity is improved by the addition of orotic acid. The orotic acid precipitates sodium and potassium ions which can interfere with the lithium ion determination.

12 Claims, No Drawings

SELECTIVITY IMPROVEMENT FOR LITHIUM ION TESTS

BACKGROUND OF THE INVENTION

The present invention relates to tests for measuring ion concentrations in aqueous solutions. More particularly, the invention relates to a method for reducing sodium and potassium interferences in tests for other ions such as lithium.

Accurate measurement of ion concentrations in aqueous solutions such as blood is very important. For example, the toxic dose levels of lithium in blood are only slightly higher than the therapeutic levels used in psychiatric treatment.

Many different methods for determining the concentration or presence of ions in solution have been developed. These include ion-specific electrodes, liquid/liquid partitioning, fluorescence enhancement, chromophore labeled ionophores, and test strips. A general discussion of each of these methods is disclosed in U.S. Pat. No. 4,670,218 which is incorporated herein by reference. These methods make use of compounds and compositions called ionophores which are molecules capable of forming a complex with a particular ion, in some instances to the substantial exclusion of other ions.

U.S. Pat. No. 4,670,218 discloses in particular a test means which comprises a porous carrier matrix substantially uniformly incorporated with (a) a homogenous hydrophobic mixture containing three principal ingredients: (1) an ionophore capable of forming a complex with a specific ion to be determined, (2) a hydrophobic substance and (3) a reporter substance capable of interacting with the complex of the ionophore and ion to produce a detectable response; and (b) a buffering substance capable of providing a pH in the range of from about 5 to 10. The patent also teaches that interferant removal substances can be incorporated into the test means.

In use, an aqueous test sample is contacted with the test means. The presence and/or concentration of the specific ion to be determined in the test sample is then determined by observing any detectable response produced. The most common reporter substances are those which cause a color change to occur.

One of the problems encountered in measuring ion concentrations is interference from other ions. For example, many of the ionophores used to complex with lithium also complex with sodium. The high concentration of sodium in serum (about 140 mM) is a serious interferant in the test for lithium concentrations in serum (about 1 mM). Accordingly, it would be a significant advancement in the art to provide a method and apparatus for measuring lithium ion concentrations in which interference from other ions is reduced or eliminated. It would be a further advancement in the art to provide such a method and apparatus which were relatively simple to perform and use. Such a method and apparatus are disclosed and claimed herein.

SUMMARY OF THE INVENTION

The measurement of the lithium ion concentration in serum is difficult because of the 100-times-greater concentration of the sodium ion. A test must be selective for 0–1.5 mM (millimolar) lithium in the presence of 140 mM sodium to avoid positive bias. The selection of an appropriate ionophore in the lithium test can provide for some of the selectivity. To further enhance the selectivity, a reagent which complexes the sodium ion is added. In the preferred embodiments of the present invention this reagent is orotic acid.

The preferred embodiment of the test means for determining the lithium ion concentration in an aqueous sample comprises a carrier matrix having a porous structure having various reagents including orotic acid incorporated therein.

The first phase incorporated in the carrier matrix includes a homogenous hydrophobic composition containing an ionophore capable of forming a complex with the lithium ions. An indicator substance capable of interacting with the lithium-ionophore complex to produce a detectable response is also included.

The second phase incorporated into the carrier matrix comprises the aqueous phase reagents. This includes a buffering substance capable of providing a pH in the range from about 6.4 to 8.5 and orotic acid in a concentration sufficient to interact with sodium and potassium ions in the sample to cause them to precipitate.

The carrier matrix is impregnated with the hydrophobic and aqueous phases by dipping the carrier matrix in solutions containing the various reagents and drying the paper at about 55° C.

In use, the aqueous test sample is contacted with the test means by any suitable method. The orotic acid in the reconstituted aqueous phase reacts with sodium and potassium ions to form a precipitate. The buffering solution maintains a substantially constant pH.

The lithium ions are free to interact with the ionophore in the hydrophobic phase to form a complex. The complex interacts with the indicator to create a detectable response such as a color change.

In another embodiment, a mixture of buffering agent and orotic acid are added to the aqueous test sample to cause the sodium and potassium ions to precipitate. A portion of the test sample is then contacted with a test means comprising a porous carrier matrix impregnated with a suitable ionophore, an indicator, and a hydrophobic substance.

DETAILED DESCRIPTION OF THE PREFERRED EMBODIMENTS

The present invention provides an apparatus and method to reduce sodium and potassium ion interference in tests for determining lithium ion concentrations.

In connection with the description of the present invention, the term "ionophore" includes molecules capable of forming a complex with a particular ion, in some instances to the substantial exclusion of others. Included in the term are coronands, cryptands, and podands.

As used in this application, the term "indicator" refers to a substance which is capable of interacting with an ionophore/ion complex to produce a detectable response such as a color change. Preferred indicators are neutral compounds having a dissociable proton which proton dissociates upon interaction of the indicator with an ionophore/cation complex. The indicator then becomes charged, effecting a change in electron distribution. The change in electron distribution produces a detectable response. The indicator substance can also be one which can trigger a detectable response together with other components. For example, the change in electron distribution in the indicator substance caused by interaction with the ionophore/ion complex can in turn facilitate the interaction of the indicator with another component which would then produce a detectable response.

The term "porous" as used herein refers to the availability of interstices in the carrier matrix which allow an aqueous test sample ready access to the hydrophobic composition containing the ionophore and the indicator substance. For example, paper is a porous carrier matrix which maintains an open lattice structure even after it has been incorporated with the homogenous hydrophobic composition and additionally with the buffering substance and orotic acid. Upon contact with the doubly incorporated and dried paper, the aqueous sample flows readily into the open network. The area of contact between the hydrophobic composition and the aqueous sample is accordingly very large.

The preferred embodiment of the present invention comprises a test means for determining the lithium ion concentration in an aqueous sample. The test means is composed of a porous carrier matrix incorporated with a homogenous hydrophobic composition and a water soluble solid phase.

The homogenous hydrophobic composition contains an ionophore capable of forming a complex with lithium ions, a hydrophobic substance and an indicator substance capable of interacting with the ionophore/ion complex to produce a detectable response such as a color change. Various types of ionophores capable of selectively interacting with lithium ion are well known to those skilled in the art. These include N,N,N',N'-tetraisobutyl-1,2-trans-cyclohexanediamide; N,N'-diheptyl-N,N'-5,5-tetramethyl-3,7-dioxanonane diamide; and N,N'-diheptyl-5,5-dimethyl-N,N'-di(3-oxapentyl)-3,7-dioxanonane diamide.

The primary function of the hydrophobic substance is to increase the detectable response of the test means by isolating the ionophore and the indicator from the aqueous phase produced by contact with the test sample. Accordingly, the substance can be a solid, liquid or a combination thereof provided that it increases the ability of the ionophore/ion complex and indicator to coexist in the homogenous hydrophobic composition. Care must be exercised to choose a substance or combination of components to act as the hydrophobic substance which does not interfere with the interaction of the ionophore/ion complex and the indicator. The selection of suitable compounds is within the skill of those of ordinary skill in the art.

Useful hydrophobic liquids include those substances which are capable of dissolving both the ionophore and the indicator. Because a liquid could dissolve or be bleached out of the test means into the aqueous sample, it is preferable that the liquid be relatively insoluble in the test sample of interest. Preferable liquids are relatively nonvolatile, having a boiling point of at least about 150° C. Such liquids are normally oxygen donors containing functional groups such as ether, ester, amide and the like.

Typical liquids which fall into this category are tricresylphosphate, dioctylphthalate, tris-2-ethylhexylphosphate, di-2-ethylhexyl sebacate, n-butylacetyl-ricinolate and nitrophenyl ethers such as 2-nitrophenyl octyl ether, 2-nitrophenyl butyl ether, dibenzyl ether and o-nitrophenyl-2-(1,3,3)trimethyl-butyl-5,7,7-triethyl octyl ether. Mixtures of these liquids can also be used.

Useful solids include cellulose/acetate, cellulose propionate, and polymers such as styrene/maleic anhydride copolymer, vinylidene chloride/acrylonitrile copolymer, styrene/allyl alcohol copolymer and poly(methylmethacrylate). Other useful polymers are poly(vinyl chloride), poly(vinylidene fluoride), polystyrene, polycarbonate, poly(4-chlorostyrene), poly(vinyl acetate), vinylidene chloride/vinyl chloride copolymer, vinyl chloride/vinyl acetate copolymer, vinyl chloride/vinyl acetate/vinyl alcohol terpolymer, polyethylene, polypropylene and polyurethane. Of course many other polymeric materials are suitable for use. The identification of such materials is well within the skill of the art.

The indicator can range in composition from a single compound which can ionize in response to the formation of the ionophore/ion complex, to a mixture of reactive species which produce a detectable product when their reaction chain is triggered by the presence of the complex. Accordingly, when no analyte-ion is present, the indicator remains dormant and no detectable response is observed. Alternatively, when the particular ion of interest is present, a complex is formed which interacts with the indicator and causes it to undergo a detectable change.

Suitable indicators include compounds such as 2-methyl-7-decyl-4-(3',5'-dichlorophen-4'-one)indonaphth-1-ol.

The water soluble solid phase comprises a buffering substance and orotic acid.

The buffering substance can be any buffer, or combination of buffers, capable of providing a pH in the range of from about 6.4 to 8.5. The buffer is chosen to facilitate the coaction of the ionophore/ion complex with preferred indicators which leads to a detectable response. The buffer is also required to maintain the pH of the aqueous phase as the sodium and potassium ions in the test sample are precipitated by the orotic acid. Suitable buffers include bis-tris propane and the like.

The orotic acid is included in the solid phase to interact with sodium and potassium ions in the aqueous sample to cause them to precipitate so as to improve the selectivity of the test. Sufficient orotic acid must be incorporated into the test means to precipitate substantially all of the sodium and potassium ions in the test sample. The determination of an appropriate amount of orotic acid is within the skill of those of ordinary skill in the art.

The test means of the preferred embodiment is formed by impregnating the porous carrier matrix with the homogeneous hydrophobic composition and the water soluble solid phase. This can easily be accomplished by dipping the porous carrier matrix into solutions of the two compositions and drying the carrier matrix.

The carrier matrix with which the homogenous hydrophobic composition is incorporated must be able to support a hydrophobic phase in such a way that substantial openings exist after drying into which an aqueous test sample can easily move. Suitable materials include paper, wood, and other cellulosic systems, sintered ceramic frits, and porous polymeric materials provided that the dimensional integrity of the matrix is maintained upon incorporation of the hydrophobic composition and subsequent contact with an aqueous sample. In addition, the matrix material must not interact with the hydrophobic composition in such a way as would interfere with the production of a detectable response.

A preferred carrier matrix is paper such as filter paper. The paper can be impregnated with the hydrophobic composition and dried. The paper can then be impregnated with the buffering substance and orotic acid. Upon contacting the test means with the aqueous test sample, the orotic acid causes the sodium and potassium ions to precipitate and the buffering substance allows the lithium ion to react with the hydrophobic phase to produce a detectable response.

In a second preferred embodiment, a test means composed of a porous carrier matrix is incorporated with a homogenous hydrophobic composition as described in the proceeding embodiment. Before the test means is contacted with the aqueous test sample, the test sample is diluted with a mixture of buffering agent and orotic acid to cause the sodium and potassium ions to precipitate.

The dilution is preferably performed at about room temperature, however, a wide range of temperatures can be used and it is within the skill of those trained in the art to determine a suitable range. The buffering agent can be any of those described above which can provide a pH in the range of from about 6.4 to 8.5.

The diluted aqueous sample is allowed to stand for a few minutes to permit the sodium and potassium ions to precipitate and then a portion of the sample is contacted with the test means to produce a detectable response indicative of the lithium ion concentration.

The following examples are illustrative of the present invention but are not meant to be limiting as to the scope thereof.

EXAMPLE 1

A series of test strips divided into two groups were prepared to show how the present invention improves the test for lithium ion by increasing the selectivity of lithium over sodium.

Whatman 31 ET paper was used as the porous carrier matrix for all the test strips. The test strips of both groups were initially dipped in a first solution containing 0.2% cellulose acetate as the hydrophobic substance 0.5% 2-methyl-7-decyl-4-(3',5'-dichlorophen-4'-one) indonaphth-1-ol as the indicator, 2.7% (N,N,N', N'-tetraisobutyl)-1,2-trans-cyclohexanediamide as the lithium ionophore and tetrahydrofuran as a solvent. The strips were then dried at 55° C.

The first group of test strips which acted as a control, were then dipped in a solution of 0.75M bis-tris propane having a pH of 8.5 to act as a buffering agent. These test strips were again dried at 55° C.

The second group of test strips were dipped in a solution of 0.75M bis-tris propane and 0.5M orotic acid having a pH of 8.5. These test strips were also dried at 55° C.

The test strips were then contacted with 30 $\mu$L samples of aqueous solutions of 35, 55, 65, 125, and 175 mM sodium chloride NaCl or 2, 5, 10, and 15 mM LiCl. The reflectance was determined between 100 to 120 seconds in K/S units at 640 nm.

The reactivity of the test means is equal to the slope of the K/S versus concentration plots. Selectivity can then be determined by dividing the reactivity with respect to lithium by the reactivity with respect to sodium. The results were as follows:

| Formula | Reactivity, R (mM$^{-1}$) | | Selectivity, R(LiCl) + R(NaCl) |
|---|---|---|---|
| | LiCl | NaCl | |
| 0 M Orotic Acid | 0.134 | 0.00889 | 15 |

-continued

| Formula | Reactivity, R (mM$^{-1}$) | | Selectivity, R(LiCl) + R(NaCl) |
|---|---|---|---|
| | LiCl | NaCl | |
| 0.5 M Orotic Acid | 0.195 | 0.000985 | 198 |

As these results show, the use of orotic acid to precipitate the sodium ion increased the selectivity of the test strips more than ten-fold.

EXAMPLE 2

In this example, orotic acid was added to the aqueous test samples to precipitate sodium ions before the test samples were contacted with the test means.

A series of test strips were prepared by dipping strips of Whatman 31 ET paper into a solution containing 0.2% cellulose acetate, 0.5% 2-methyl-7-decyl-4-(3',5'-dichlorophen-4'-one)indonaphth-1-ol 2.7% (N,N,N', N'-tetraisobutyl)-1,2-transcyclohexanediamide, and tetrahydrofuran. The test strips were then dried at 55° C.

Aqueous solutions with 0, 5, 10, 15, and 20 mM LiCl or 125, 175, 225, 500 mM NaCl were diluted 1:3 with 0.75M bis-tris propane and 0.5M orotic acid, at a pH of 8.5 at room temperature (about 23° C). After a few minutes, 30 microliters of each solution was added to the dried impregnated paper. The reflectance was determined between 100 to 120 seconds in K/S units at 640 nm.

A second set of aqueous solutions with 0, 5, 10, 15, and 20 mM LiCl or 125, 175, 225, 500 mM NaCl were diluted 1:3 with 0.75M bis-tris propane at a pH of 8.5 at room temperature. After a few minutes, 30 microliters of each of these solutions was added to the dry impregnated test strips. The reflectance was determined between 100 and 120 seconds in K/S units at 640 nm.

Selectivity can be determined by dividing the reactivity with respect to lithium by the reactivity with respect to sodium. The following results were obtained:

| Diluent Solution | Reactivity, R (mM$^{-1}$) | | Selectivity, R(LiCl) + R(NaCl) |
|---|---|---|---|
| | LiCl | NaCl | |
| 0 M Orotic Acid | 0.196 | 0.00822 | 24 |
| 0.5 M Orotic Acid | 0.287 | −0.000299 | >287 |

As can be seen from these results, the selectivity of the test strips with respect to lithium increased over ten-fold when the orotic acid was added to the aqueous test samples before they were contacted with the test strips.

While the invention has been described with respect to the presently preferred embodiments, it will of course be appreciated by those skilled in the art that modifications or changes could be made without departing from the scope or spirit of the invention. For example, the use of orotic acid could also be adapted to other types of test procedures such as ion-specific electrodes, liquid/liquid partitioning, and chromophore/labeled ionophores to increase their selectivity. Accordingly, all modifications or changes which come within the meaning and range of equivalency of the claims are to be embraced within their scope.

What is claimed is:

1. A test means for determining lithium ion concentration in an aqueous sample, the test means comprising a carrier matrix having a porous structure substantially uniformly incorporated with:

a homogenous hydrophobic composition containing an ionophore capable of forming a complex with lithium ions, an indicator substance capable of interacting with the lithium/ionophore complex to produce a detectable response and a hydrophobic substance;

a buffering substance capable of providing a pH in the range of from about 6.4 to 8.5; and orotic acid in a concentration sufficient to interact with sodium and potassium ions in the sample to precipitate them.

2. A test means for determining lithium ion concentration in an aqueous sample as defined in claim 1 wherein the porous carrier matrix comprises paper.

3. A test means for determining lithium ion concentration in an aqueous sample as defined in claim 1 wherein the indicator is capable of producing the appearance of or a change in color in the presence of the lithium/ionophore complex.

4. A test means for determining lithium ion concentration in an aqueous sample as defined in claim 1 wherein the hydrophobic substance is cellulose acetate.

5. A test means for determining lithium ion concentration in an aqueous sample as defined in claim 1 wherein the ionophore is (N,N,N',N'-tetraisobutyl)-1,2-trans-cyclohexanediamide.

6. A method for determining lithium ion concentration in an aqueous sample, said method comprising:

mixing the aqueous sample with orotic acid such that sodium and potassium ions in the sample are precipitated;

contacting the aqueous sample with a hydrophobic composition containing an ionophore capable of forming a complex with lithium and an indicator capable of interacting with the lithium/ionophore complex to produce a detectable response; and measuring the response.

7. A method for determining lithium ion concentration in an aqueous sample as defined in claim 6 wherein the mixing and contacting steps are accomplished simultaneously by applying the aqueous sample to a carrier matrix having a porous structure containing the orotic acid and the hydrophobic composition.

8. A method for determining lithium ion concentration in an aqueous sample as defined in claim 6 wherein the mixing step comprises adding orotic acid and a buffering substance to the aqueous sample.

9. A method for determining lithium ion concentration as defined in claim 8 wherein the contacting step comprises applying the aqueous sample to a carrier matrix having a porous structure containing the hydrophobic composition.

10. A method of reducing sodium ion interference in a lithium ion test comprising:

mixing orotic acid with an aqueous phase containing the sodium ions to form a precipitate.

11. A method of reducing sodium ion interference in a lithium ion test as defined in claim 10 wherein the orotic acid is deposited as a solid phase on a test strip.

12. A method of reducing sodium ion interference in a lithium ion test as defined in claim 10 wherein the pH of the aqueous phase is maintained between about 6.4 and 8.5.

* * * * *